United States Patent [19]

Klein et al.

[11] Patent Number: 5,293,213
[45] Date of Patent: Mar. 8, 1994

[54] UTILIZATION OF A MODULATED LASER BEAM IN HETERODYNE INTERFEROMETRY

[76] Inventors: Uwe K. A. Klein, King Fahd University of Petroleum and Minerals Box 546; Joseph N. Mastromarino, King Fahd University of Petroleum and Minerals Box 641; Abdul-Aziz A. Suwaiyan, King Fahd University of Petroleum and Minerals Box 625, all of Dhahran, Saudi Arabia, 31261

[21] Appl. No.: 929,155

[22] Filed: Aug. 12, 1992

[51] Int. Cl.$^5$ .............................................. G01B 9/02
[52] U.S. Cl. ..................................... 356/349; 356/318; 250/458.1; 250/459.1
[58] Field of Search ......................... 356/344, 346, 318; 250/458.1, 459.1, 461.1, 461.2, 338.5

[56] References Cited

U.S. PATENT DOCUMENTS

| | | | |
|---|---|---|---|
| 3,817,622 | 6/1974 | Billman et al. | 356/73 |
| 4,198,567 | 4/1980 | Eneroth et al. | 250/459.1 |
| 4,243,318 | 1/1981 | Stohr | 356/39 |
| 4,460,274 | 7/1984 | Schumann et al. | 356/318 |
| 4,461,573 | 7/1984 | Lucht et al. | 356/318 |
| 4,479,499 | 10/1984 | Alfano | 128/665 |
| 4,490,040 | 12/1984 | Lucht et al. | 356/318 |
| 4,840,485 | 6/1989 | Gratton | 356/317 |
| 5,022,757 | 6/1991 | Modell | 356/318 |

OTHER PUBLICATIONS

K. J. Williams et al., "6-34 GHz Offset Phase-Locking of Nd:YAG 1319 nm Nonplanar Ring Lasers", Electronics Letters, Aug. 31, 1989, vol. 25, No. 18, pp. 1242-1243.
K. J. Williams et al., "High Frequency Microwave Phase Response Measurement Technique for Optical Input-Output Devices", CLEO 90/Tuesday Poster, No. CTUH75, pp. 152-154.
E. Miron et al., "Continuous Scanning of Atomic Uranium Levels", Optical Communications, Sep. 1976, vol. 18, No. 4, pp. 536-538.
N. Omenetto et al., "Laser-Induced Intermodulated Flame Fluorescence: A New Approach to Scattering Correction in Analytical Atomic Fluorescence", Applied Spectroscopy, vol. 38, No. 5, 1984, pp. 619-624.
E. Gratton et al., "A Continuously Variable Frequency Cross-Correlation Phase Fluorometer with Picosecond Resolution", Biophysical Journal, 1983, vol. 44, pp. 315-324.
E. Gratton et al., "Multifrequency Phase and Modulation Fluorometry", Ann. Rev. Biophys. Bioeng. 1984, vol. 13, pp. 105-124.
E. Gratton, "Multifrequency Phase Fluorometry Using Pulsed Sources: Theory and Applications", Spectroscopy, vol. 1, No. 6, 1986, pp. 28-38.
J. R. Alcala et al, "A Multifrequency Phase Fluorometer Using the Harmonic Content of a Mode-Locked Laser", Analytical Instrumentation, 14 (3 and 4), 1985, pp. 225-250.
D. M. Jameson et al., "The Measurement and Analysis of Heterogeneous Emissions by Multifrequency Phase and Modulation Fluorometry", Applied Spectroscopy. Reviews, 1984, 20(1), pp. 55-106.

(List continued on next page.)

Primary Examiner—Samuel A. Turner
Assistant Examiner—LaCharles P. Keesee
Attorney, Agent, or Firm—Cumpston & Shaw

[57] ABSTRACT

Two laser beams of different frequencies are combined to form a composite carrier beam of a frequency midway between those of the individual beams and modulated at the beat frequency between the individual beams. This composite beam can be used in a variety of ways, such as to irradiate a workpiece, the electro-optical frequency response characteristics of which are to be studied. By using an autocorollation technique the range of frequency over which these characteristics can be studied has for the first time been greatly expanded, well up into the terahertz range. Other applications of the equipment include the fine measurement of distances in the micrometer to meter range and secure digital transmission of data on a laser beam.

32 Claims, 5 Drawing Sheets

OTHER PUBLICATIONS

U. K. A. Klein, "Picosecond Fluorescence Decay Studies by Phasefluorometry and its Application to the Measurement of Rotational Diffusion in Liquids", The Arabian Journal for Science and Engineering, 1984, vol. 9, No. 4.

S. Haroche, "Quantum Beats and Time-Resolved Fluorescence Spectroscopy", High Resolution Laser Spectroscopy by Springer Verlag, Berlin, 1967, pp. 253–257.

Signal Analyzers manufactured by Hewlett-Packard under numbers HP8565B, HP8567A and HP8568B.

"Pulsed Ion and Dye Laser Accessories-Model 409 Scanning Autocorrelator" marketed by Spectra-Physics.

"Model 390 Angle Tuned Frequency Doubler" marketed by Spectra-Physics.

UTILIZATION OF A MODULATED LASER BEAM IN HETERODYNE INTERFEROMETRY

FIELD OF THE INVENTION

This invention relates to novel utilization of a beating laser beam formed from a combination of two laser beams of different frequencies that have been so brought together that they effectively constitute a resultant carrier beam modulated at the beat frequency, i.e. the difference between the individual frequencies of the two beams.

BACKGROUND OF THE INVENTION

Practical applications for such a modulated laser beam include the study of the molecular (or atomic) properties of materials or other workpieces. Throughout this specification and claims the term "workpiece" will be used to cover simple materials, such as chemical elements or compounds, as well as more complex structures, such as electronic devices, that may be under study. When the workpieces studied include individual chemical elements or chemical compounds they may be in solid, liquid or gaseous phase.

The studied properties of the workpieces may include optical absorption characteristics; the lifetime or decay characteristics of various forms of luminescence, such as fluorescence or phosphorescence; photochemical or photophysical characteristics; the optical characteristics of electronic components, especially those used as optical detectors, such as photodiodes and photomultiplier tubes; and may also include electrical characteristics, such as the resistivity of an electronic component, e.g. a semiconductor, when such component is exposed to light.

Any of these characteristics may take the form of either or both of amplitude or phase variations with frequency. In a primary application according to the invention it is an objective to obtain details of these characteristics as a function of the frequency of light applied to the workpiece.

Other utilizations for a modulated laser beam according to the present invention include the measurement of distances including very short distances, e.g. between one micrometer and one meter, and the development of a frequency or phase modulated communications technique, as will be explained in more detail below.

PRIOR ART

It is known to combine two laser beams of different frequencies and hence generate a beat frequency. For example, K. J. Williams et al. in "6–34 GHz Offset Phase-Locking of Nd:YAG 1319 nm Nonplanar Ring Lasers" published in Electronics Letters, Aug. 31, 1989, Vol. 25, No. 18, pp 1242-3 (hereinafter referred to as Williams et al. (89)), disclose a system that contains two lasers, collimated output beams from which are heterodyned to achieve a beat frequency having a maximum of the order of 34 GHz. The beat frequency is tunable by varying the frequency of one of the lasers. The other laser has no provision for varying its frequency. The system generates very stable microwaves and is said to have utility in phase array radar, optical distribution of microwave signals and optical pulse synthesis. In a subsequent paper, namely "High Frequency Microwave Phase Response Measurement Technique for Optical Input-Output Devices" published in CLEO 90/TUESDAY POSTER, under No. CTUH75, pp 152-4 (hereinafter referred to as Williams et al. (90)), K. J. Williams et al. disclose a system for using the circuit shown in Williams et al. (89) for measuring the microwave phase and amplitude response of optical input-optical output devices, such as an optical amplifier to be used as a broadband amplifier. The paper also discloses the measurement of the phase and amplitude response of a photodiode.

A so-called multiphoton technique is also known. An example of this technique is provided by E. Miron et al. in "Continuous Scanning of Atomic Uranium Levels" published in Optics Communications, Vol. 18, No. 4, pp 536-8, September 1976. This paper discloses the use of two tunable pulsed lasers whose pulsed beams are combined and used to irradiate uranium vapour. The first pulsed laser beam serves to elevate some of the uranium atoms from a first to a second energy level, and the second pulsed laser beam serves to further elevate some of these elevated atoms from the second to a third energy level. The method is said to be useful for discovering and assigning high odd levels of atomic uranium, 62 such levels having been detected in the region of 33580–34400 cm$^{-1}$, for example. Although the pulsed laser beams are of different mean frequencies, beat frequencies between them are not utilized in this process. The primary pulsed laser beams act independently of each other to elevate atomic populations between a different pair of energy levels, i.e. between levels 1 and 2 for one pulsed beam, and between levels 2 and 3 for the other pulsed beam.

N. Omenetto et al. in "Laser-Induced Intermodulated Flame Fluorescence: A New Approach to Scattering Correction in Analytical Atomic Fluorescence" published in Applied Spectroscopy, Vol. 38, No. 5, 1984, pp. 619–624, disclose a technique of intermodulated fluorescence in analytical flame fluorescence using two laser beams of the same frequency that are amplitude modulated by choppers at different frequencies and are then counterpropagated collinearly through an atomizer. The difference frequency of the two modulation frequencies is then used to modulate an element of interest for the purpose of spatially resolved combustion diagnostics.

U.S. Pat. No. 5,022,757 issued Jun. 11, 1991 to M. D. Modell generates two beams from a single laser, one such beam being passed through a frequency shifter, such as a Bragg cell. The two beams, now of different frequencies, are caused to intersect within a medium carrying a target substance that establishes a sensing volume. The result is generation of a beat frequency at the sensing volume. Means are provided for detecting a selected optical effect, e.g. absorbance or fluorescence, of the target substance, which latter may be a photodynamic sensitizer selectively retained within a tumour or other target tissue within a patient, and for generating a signal representative of such selected optical effect. A filter passes only the portion of this signal that is substantially at the beat frequency. This portion is then combined with a selected value to determine the amount and location of the target substance. In this arrangement there is no need for and hence no provision for tuning either of the laser beams, since the system operates with a selected beat frequency that remains unchanged throughout. The effect is not to determine the properties of the workpiece as a function of the beat frequency. Indeed any variation of the response to the beat frequency would render more difficult the determining of the size and location of the target.

Since the present application is concerned, inter alia, with fluorometry and the measurement of the lifetime or decay characteristics of various forms of luminescence, it will be convenient at this stage, in order to avoid the need for this specification to include details of this known art, to provide the following references to fluorometry generally (the disclosures of which references are incorporated herein by reference).

Specifically, the general state of the art of phase fluorometry for lifetime and dynamics measurements of excited states is given by the following literature:

1. E. Gratton and E. Gratton et al.
   (a) A Continuously Variable Frequency Cross-Correlation Phase Fluorometer with Picosecond Resolution, published in biophysical Journal, Vol. 44, 1983, pp 315-324;
   (b) Multifrequency Phase and Modulation Fluorometry, published in Ann. Rev. Biophys. Bioeng. 1984.13, pp 105-124;
   (c) Multifrequency Phase Fluorometry Using Pulsed Sources: Theory and Applications, published in Spectroscopy, Vol. 1, No. 6, 1986, pp 28-38;
2. J. R. Alcala et al; A Multifrequency Phase Fluorometer using the harmonic content of a mode locked laser, published in Analytical Instrumentation, 14 (3 and 4) pp 225-250, 1985; and
3. D. M. Jameson et al; The Measurement and Analysis of Heterogeneous Emissions by Multifrequency Phase and Modulation Fluorometry, published in Applied Spectroscopy Reviews, 20(1), pp 55-106, 1984.
4. U.K. A. Klein; Picosecond Fluorescence Decay Studied by Phasefluorometry and its Application to the Measurement of Rotational Diffusion in Liquids, published in The Arabian Journal for Science and Engineering, Vol. 9, No. 4, 1984.
5. S. Haroche Quantum Beats and Time-Resolved Fluorescence Spectroscopy, published in High Resolution Laser Spectroscopy by Springer Verlag, Berlin, 1976 (note especially pp 253-257 and FIG. 7.2a).

It will be noted that the art of phase fluorometry as summarized in these references essentially employs either a single, sometimes tunable, laser beam or a pair of laser beams of fixed frequencies. Beat frequencies have not previously been utilized to achieve frequency dependent measurements.

Essentially the same comment is applicable to the nearest patent references of which applicants are aware, namely U.S. Pat. Nos.:
(a) 3,817,622 issued Jun. 18, 1974 to K. W. Billman et al.;
(b) 4,198,567 issued Apr. 15, 1980 to Eneroth et al.; 4,243,318 issued Jan. 6, 1981 to M. Stohr;
(d) 4,460,274 issued Jul. 17, 1984 to H-J. Schumann et al.;
(e) 4,461,573 issued Jul. 24, 1984 to H. Lucht et al;
(f) 4,479,499 issued Oct. 30, 1984 to R. R. Alfano (note the reference at the top of column 6 to the alternative use of lasers);
(g) 4,490,040 issued Dec. 25, 1984 to H. Lucht et al; and
(h) 4,840,485 issued Jun. 20, 1989 to E. Gratton; and finally
P.C.T. application WO90/09575 of G. W. Mitchell, published Aug. 23, 1990.

SUMMARY OF THE INVENTION

A feature of one aspect of the present invention is the provision of a modulated (beating) carrier laser beam that can elevate the energy level of a population of molecules (or atoms) in a workpiece in such a way that, when this energy is re-emitted to return some or all of the elevated population to a lower energy level, the resulting secondary emission will be modulated at the beat frequency. Varying the beat frequency while examining this secondary emission will provide data on the frequency dependent characteristics of the molecules (or atoms) of the workpiece.

At normal temperatures the populations under study will usually be populations of molecules, but they may be populations of atoms, especially when the material under study is at a high temperature, and hence the expression "molecules (or atoms)" will be used throughout this specification and claims in the absence of a convenient generic term to cover these two possibilities.

More specifically, the invention in a first aspect can be defined as a method of observing an electro-optical frequency response characteristic of a portion of a workpiece, comprising irradiating a molecular (or atomic) population of such workpiece portion with a first laser beam having a first wavelength in a range of approximately 250 to 4000 nm; varying this first wavelength to bring it within an absorption curve of the workpiece portion and hence cause elevation of at least some of said population from a first energy level to a second energy level; and detecting this elevation of population, e.g. by detecting a response from the workpiece portion in the form of a secondary optical emission resulting from decay of at least some of the elevated population to a lower energy level, e.g. the first energy level. This first response will have a characteristic that corresponds to that of the first laser beam (if the laser beam is a steady, continuous beam, the response will be likewise steady; if the beam is pulsed, the response will be pulsed). Other methods of achieving this detection of the population elevation include measuring the electrical conductivity of a semiconductor workpiece, or measuring an absorption related to the population at the second energy level.

Simultaneously with this irradiation of the workpiece portion by the first beam, the method includes irradiating the same workpiece portion with a second laser beam that has a second wavelength in the same range but different from the first wavelength. Upon detection of the first response indicative of the population elevation caused by the first beam, the second wavelength is varied as necessary to bring it within the same absorption curve of the workpiece portion and hence to cause a further molecular (or atomic) population to be elevated from the same first energy level to the same second energy level. As a result the combined elevated population in the second energy level effectively experiences irradiation by both the beams simultaneously, and, at the same time, amplitude modulation at a beat frequency equal to the difference between the first and second wavelengths. This is equivalent to these populations experiencing irradiation by a carrier beam of a mean frequency halfway between the first and second wavelengths modulated at the beat frequency.

The method includes detecting this amplitude modulation, e.g. by detecting by one of the foregoing methods the fact that the response from the workpiece portion no longer has simply the characteristic of the first laser beam, but is now modulated at the beat frequency. Upon detection of this second and modulated response, at least one of the first and second wavelengths is varied to vary the beat frequency, while maintaining both wavelengths within the absorption curve. Alternatively, the first and second wavelengths can be varied in tandem in order to hold the beat frequency constant while varying the mean (carrier) frequency. A characteristic of the modulated response is then measured as a function of at least one of the beat frequency and the mean frequency. This characteristic will typically be either or both of the relative amplitude and the relative phase of the modulated response as a function of frequency (the beat and/or the mean frequency). Plots of these characteristics provide valuable information on the nature, particularly fluorescent lifetimes or more complex decays, of the workpiece, as explained in the literature referred to above.

A further aspect of the invention relates to the application of the present technology to an autocorollation technique in which two incoming modulated beams are multiplied together to generate an average value in a detector that cannot directly follow the high frequencies involved, e.g. in the terahertz range. The incoming beams may be two portions of the modulated carrier beam that has been split into these two portions, or one of the incoming beams may be derived from the second response from the workpiece, which response beam is then multiplied by the carrier beam. In each instance a variable time delay is introduced into one of the beams being multiplied together, and either or both of the beat and mean frequencies can also be varied as needed.

As more fully described below, the first of these techniques (multiplying two portions of the carrier beam together) can be used to measure the beat frequency, to measure the length of the delay and hence the physical thickness of an element generating such delay, or to form a digital communication system.

As also described in detail below, the second technique (multiplying the response beam with the carrier beam) provides an especially valuable research tool, because it enables the system to measure the degree of modulation and the phase shift of the workpiece response as a function of frequency over a range that has not hitherto been possible because of the practical frequency limitations of existing photodetecting equipment. In fact, beat frequencies of up to 70 THz have been measured.

The invention also consists of apparatus for carrying out methods of the invention.

DETAILED DESCRIPTION OF THE DRAWINGS

In the drawings.

DESCRIPTION OF THE PREFERRED EMBODIMENTS OF THE INVENTION

Figures 1, 6:
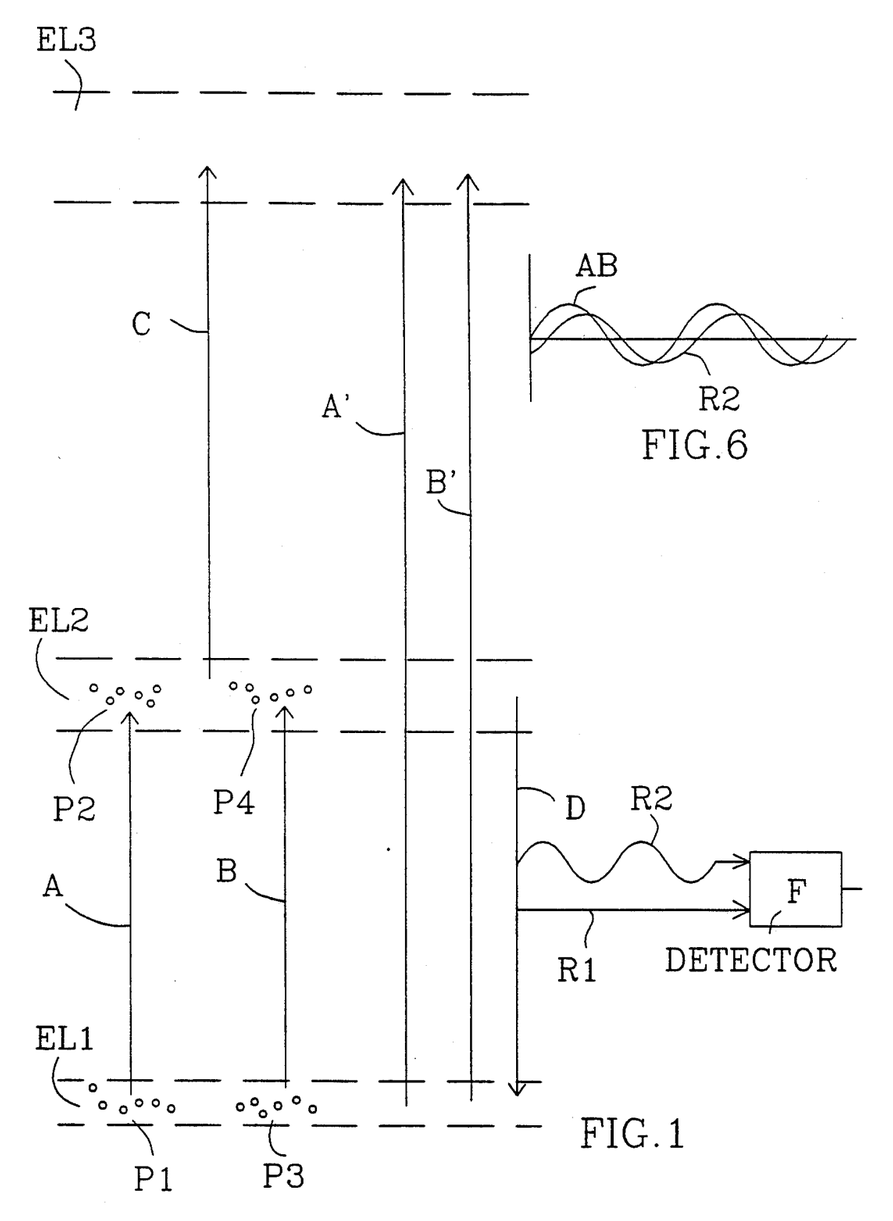
FIG. 1 is a diagram of energy levels of molecular (or atomic) populations in a workpiece.
FIG. 6 shows the relative phases of a beating laser

Referring first to FIG. 1, there are here illustrated three molecular (or atomic) energy levels of a workpiece position under study, designated EL1, EL2 and EL3, respectively. The level EL1 will usually be the ground level, but not necessarily so. Due to the uncertainty principle, it is impossible to define exactly the boundaries of these levels. The shorter the lifetime of a level is, the broader are its boundaries.

Arrow A in FIG. 1 designates the energy pumping effect of a first laser beam A on a population P1 of molecules (or atoms) to elevate some of them from the energy level EL1 to the energy level EL2 as an elevated population P2. In a like manner, the arrow B designates a similar effect that results from a second laser beam B, i.e. pumping some of a population P3 to become population P4. Arrows A' and B' show how similar pumping by the respective beams (with higher energies) could take place to the level EL3. In a like manner (not shown) the beams could each pump populations from level EL2 to EL3. The essential concern is that the beams A and B (or A' and B') both have frequencies such that they fall within an absorption curve Y of the workpiece shown in FIG. 2. As a result, the unpumped populations P1 and P3 both begin at the same energy level as each other, e.g. level EL1, and the elevated populations P2 and P4 both exist at the same energy level as each other, e.g. level EL2. Only under these conditions, i.e. with both beams elevating populations between the same two energy levels, will the molecules (or atoms) of the elevated populations simultaneously experience both the laser beams A and B and the combined effect of these beams, namely the carrier AB which will be modulated at the beat frequency as shown in FIG. 3. As this figure shows the beams A and B are assumed to be continuous and to have the same power as each other, taken as unity, while the workpiece experiences the equivalent of the carrier AB of the mean frequency, which is amplitude modulated between powers 0 and 2 at the beat frequency.

Figure 2:
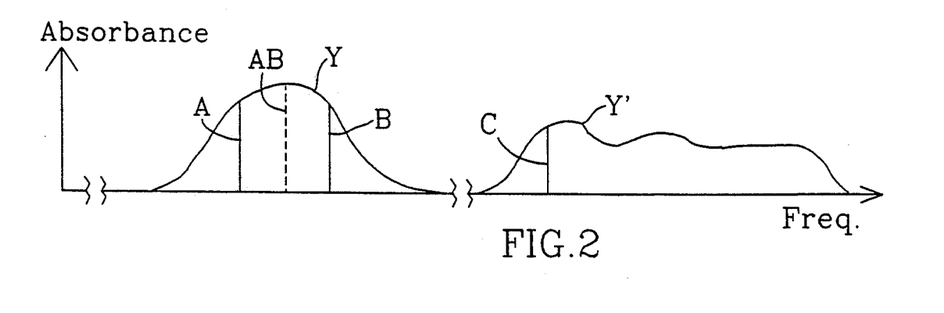
FIG. 2 is an absorbance/frequency diagram of a typical molecular (or atomic) absorption curve.
Figure 3:
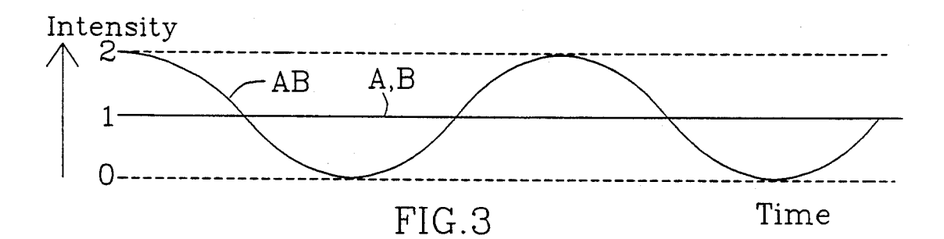
FIG. 3 illustrates the formation of a beating beam from a combination of individual input beams.

As shown in FIG. 2, if the beam B were replaced by a beam C of a frequency outside the absorption curve Y, it might fall within another absorption curve Y' and hence achieve some pumping, e.g. between levels EL2 and EL3 as shown in FIGS. 1 and 2, but the beat frequency between the beam C and the beam A would not be experienced by the workpiece. It is important to stress that, for a given population at a given energy level to experience the beating beam, the molecules (or atoms) of the elevated population or populations must both begin at the same level and be pumped simultaneously to the same level. This limitation is important, because it distinguishes the present invention from prior work in the field of multiphoton technique. Also, in multiphoton techniques pulsed lasers are used. See the Miron et al. reference mentioned above.

Figure 4:
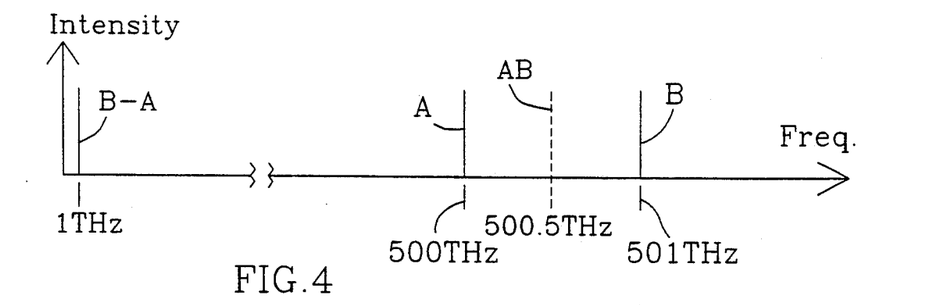
FIG. 4 is an intensity/frequency diagram showing typical individual input beams and a combined (beating) beam.

FIG. 4 illustrates an example of a pair of laser beams A and B with respective frequencies of 500 and 501 THz (a terahertz is $10^{12}$ Hz; 1200 THz is equivalent to a wavelength of approximately 250 nm, and 75 THz is equivalent to approximately 4000 nm). In this example the carrier beam AB has a frequency of 500.5 THz and the modulation frequency B - A is 1 THz. Other examples are a combination of the beam A with a beam B having a frequency of 500.000001 THz, to yield a carrier modulated at 1 MHz, or a combination of the beam A with a beam B of frequency 570 THz, to yield a carrier modulated at 70 THz.

Figure 5:
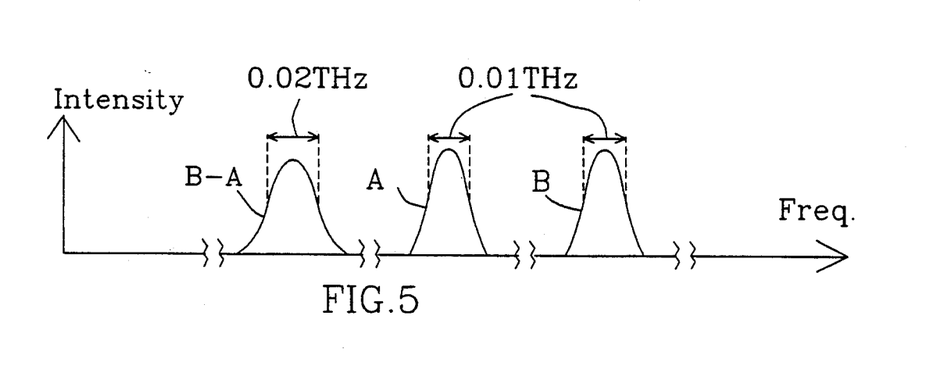
FIG. 5 is similar to FIG. 4 while illustrating the effect of using lasers with lower quality beams.

While FIG. 4 assumes the use of ring lasers or other lasers of high quality that produce very narrow band width beams, it is one of the advantages of the present invention that in many instances, e.g. when the beat frequency is relatively high, it can tolerate much wider single mode line widths and hence can be performed with less costly lasers. Such wider line width beams are shown in FIG. 5 which is a variant of FIG. 4 showing laser beams A and B and the beating frequency B - A, each with a relatively large beam width, e.g. 0.01 THz in the case of the beams A and B, and 0.02 THz in the case of the frequency B - A.

In a first method of operation, the laser producing the beam A is initially tuned to bring its frequency to a location within the absorption curve Y, i.e. the situation shown in FIG. 2 but without the beam B being considered. The molecular (atomic) population P1 is thus excited by this beam A to a higher energy level, e.g. to level EL2, population P2. This population decays in the normal manner to re-emit the energy as a secondary emission shown symbolically by the line D in FIG. 1. This secondary emission will often be at a different frequency from that of the primary exciting beam, and does not itself take the form of a beam, but is random in direction and will require to be collected by a suitable detector and possibly amplified. Assuming that the beam A is a steady continuous beam and that as a result the elevating process that it produces maintains a substantially stable population P2 in level EL2, the secondary emission of the decay D, which has been shown as a response R1 in FIG. 1, also has a substantially steady state intensity. This response R1 is detected in a detector F. The output from this detector tells the operator (which may be a computer) that the beam A has found an absorption curve, such as the curve Y, in the workpiece portion under study. There may in fact be many such absorption curves along the spectrum in most workpieces, but for the purposes of the present explanation the curve Y will be assumed to be the one that is found by the initial turing of the beam A.

The operator then applies the beam B to substantially the same location in the workpiece and tunes it to a frequency that will be expected to bring it also within the curve Y. The shape of the frequency response of absorption curves like the curve Y will vary greatly, depending on the nature of the workpiece, and the operator's knowledge of typical curve shapes for the workpiece under study will be helpful in tuning the beam B. As mentioned above in regard to FIG. 4 the spacing between the frequencies of the beams A and B may be chosen to be within a very wide range, including, for example, from as small as 1 MHz to as high as 70 THz, provided that the width of the absorption curve Y permits.

As soon as the beam B has been brought into the same absorption curve Y of the workpiece as the beam A, the population no longer experiences the effects of the individual beams A and B but that of the modulated carrier AB, so that the secondary emission D now takes the form of a modulated response R2 as shown in FIG. 1. This response R2 actually takes the form of a carrier of a frequency determined by characteristics of the workpiece modulated at the beat frequency at an amplitude and phase that represents a response characteristic of the workpiece. The response R2 is seen by the detector F. FIG. 6 shows how the response R2 has the same modulation frequency (beat frequency) as the carrier AB, but with some lag in phase (the carrier frequency of R2 may be the same as or different from that of AB). The relative intensities are exaggerated in FIG. 6; in practice the intensity of the response R2 may typically be tow or three orders of magnitude less than the intensity of the carrier AB.

The description so far has assumed the use of CW lasers, preferably ring lasers that generate high quality (narrow band width) beams, although, as has been explained, at the higher beat frequencies the band width becomes less important and cheaper lasers producing lower quality beams can be used. It is, however, also possible to use pulsed lasers, especially when high power is needed, subject to ensuring that the pulses overlap in the workpiece. For many workpieces high power is unnecessary, so that CW lasers are usually preferred, since they avoid the problem that a pulse is a combination of a very large number of frequencies. Pulsed lasers will still generate a beat frequency similar to that shown in FIG. 4 or 5 and a modulated response R2 as shown in FIG. 6 but divided into separate portions, one portion for each pulse, it being assumed that the pulse length is very large compared to the wavelengths of the lasers.

Figure 7:
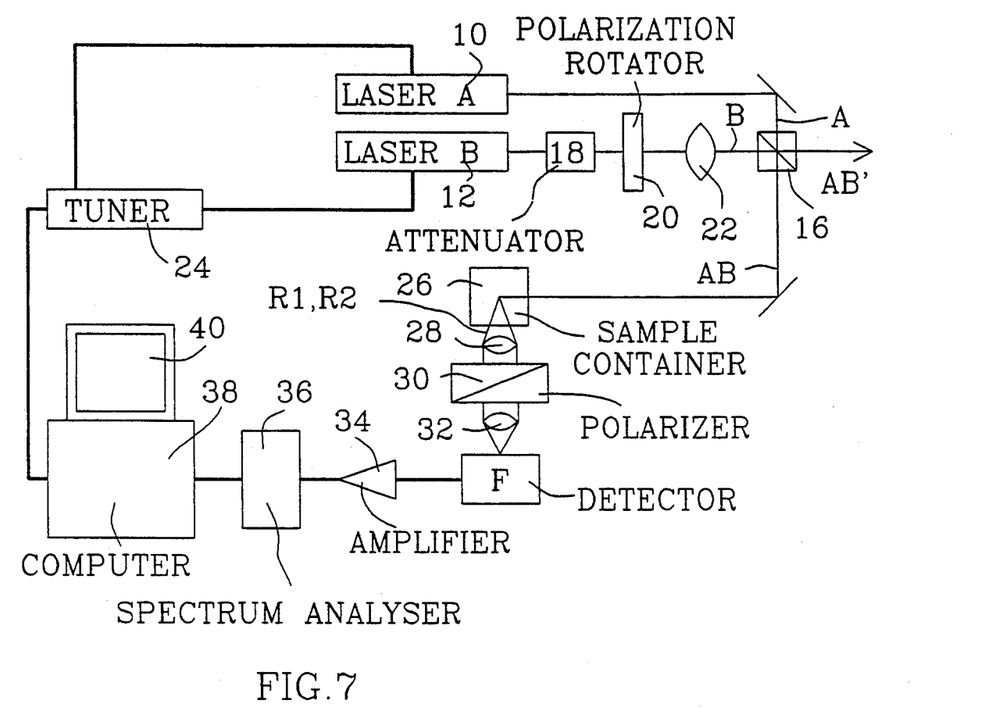
FIG. 7 is a block diagram showing an assembly of optical and electrical components that can be employed for carrying out one preferred embodiment of a method of the invention.

FIG. 7 shows an example of an arrangement for practising one embodiment of the invention. A pair of CW lasers 10 and 12 produce beams A and B that are combined in a double partial mirror device 16 to form the carrier beam AB and a similar beam AB'. A polarization rotator 20, an attenuator 18 and a divergence adjusting lens system 22 are used to ensure as near perfect as possible superposition of the beams A and B on each other with identical amplitudes, polarization and physical shapes and dimensions. Each laser can be tuned individually by a tuner 24 to achieve the desired frequency, either manually or under the control of a computer 38.

The carrier beam AB is applied first to a workpiece sample under study in a container 26, and some of the secondary emission response R1 or R2 is collected by a lens 28 and, after passing through a polarizer 30, is focused by a lens 32 on the detector F which will typically be a photodiode or a photomultiplier tube. The output of the detector F passes through an amplifier 34 and a spectrum analyzer 36 to the computer 38 having a screen 40. The spectrum analyzer is a known instrument, for example one of the Signal Analyzers manufactured by Hewlett-Packard under numbers HP8565B, HP8567A and HP8568B.

Figure 8:
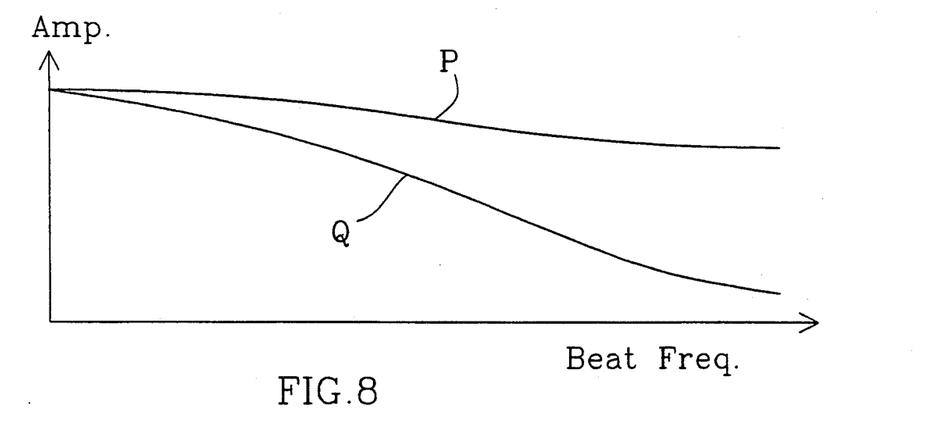
FIG. 8 shows a typical output diagram that can be produced by such method.

As indicated above, the secondary emission will either be absent (when neither of the beams A and B is within the curve Y) a steady response R1 (when only one of the beams A and B is within the curve Y), or a modulated response R2 when both the beams A and B have frequencies that bring them within the same curve Y. To achieve this latter result both of the two beams will be individually tuned to achieve a modulated response that is recognized by the detector F and measured by the spectrum analyzer 36 and the computer 38. Having thus obtained the modulated response R2, the operator now further tunes one or other, or both, of the lasers 10, 12 to vary the beat frequency while nevertheless keeping both the primary frequencies within the curve Y, a fact that can be monitored by continuing to observe the existence of the modulated response R2. As a result the computer is able to display on its screen 40 a curve Q for the amplitude response of the reference sample as a function of the beat frequency, as shown in FIG. 8. The sample is now replaced by a reference scatterer to generate a curve P by duplicating the steps that produced the curve Q. This reference scatterer will normally have been so chosen as itself to have as far as possible a flat amplitude/frequency response, so that the changes in the amplitude of the curve P with frequency are not the result of the nature of the scatterer, but rather the effect of a change of performance with frequency of the electronic components downstream of the container 26, principally the components in the detector F.

The function of the reference scatterer is to scatter the beam AB to resemble the fluorescence or any other emission of the sample under study, in order to determine a reference for the modulation and phase angle at the container 26, and hence the modulation and phase response of the detection system. The scattered light (not emission) is always modulated at the beat frequency with the same modulation depth as the beam AB, provided the scatterer does not absorb and reemit light. For example a milk solution is an excellent scatterer above 500 nm. Below 500 nm magnesium oxide powder suspended in water is a good scatterer. It is also possible to use a workpiece with a known response in place of a scatterer. However, a scatterer is preferred as the scattering is, ideally, independent of frequency over a wide wavelength range, and any changes in the response curve P from a straight line are then due only to the frequency dependence of the apparatus.

If it is proven that over the range of interest there is no significant change with frequency of the components downstream of the container 26, this step of using a reference scatterer can be omitted.

As indicated above, it may also be revealing of the characteristics of the workpiece to hold the beat frequency unchanged while varying the carrier frequency. This procedure will generate different curves of the response of the reference sample and/or workpiece.

The result (quotient) of curve Q divided by curve P represents the true frequency dependency of the workpiece sample under study, this being the information required, because it can be used to obtain many of the optical properties enumerated above.

FIG. 8 shows the amplitude/frequency response of the workpiece. It is also possible to measure and produce similar curves of the phase shift responses of the reference scatterer and of the workpiece sample under study as a function of frequency, which likewise provide the researcher with valuable data. The true phase shift of a workpiece sample is obtained by taking the difference between the equivalent curves for P and Q relating to phase shift measurements.

The procedure for generating the amplitude curves of FIG. 8 (or the equivalent phase curves) can thus be summarized as follows:
1. Place a workpiece sample in the container 26.
2. Tune the beam A to achieve a steady response R1, i.e. to locate this beam in the curve Y.
3. Tune the beam B to achieve a modulated response R2, i.e. confirming that the beam B is also in the curve Y.
4. Tune one or both of the beams A and B to vary the modulation (beat) frequency or the carrier frequency, while maintaining both of the individual beam frequencies within the curve Y, i.e. within a range that continues to produce the modulated response R2, whereby to enable measurement of the amplitude curve Q (or an equivalent phase curve, and/or equivalent curves of variations with carrier frequency).
5. If it is required to determine the frequency response of the apparatus, replace the workpiece sample with the reference scatterer.
6. Repeat steps 2, 3 and 4 to generate curve P (and/or its equivalents as above), and hence determine the frequency dependence of the electronic components of the apparatus.

While FIG. 7 shows the preliminary superposition of beams A and B on each other to produce the composite carrier beam AB prior to irradiation of the workpiece, this being the preferred method, it is also possible to achieve a similar situation in which the irradiated molecular (or atomic) population experiences the modulated carrier to produce a modulated response, if the beams are separately directed onto the portion of the workpiece under study so that they effectively combine in the workpiece and simultaneously irradiate the same molecular (or atomic) population.

One of the important features of the present arrangement is the extremely wide frequency range that it can potentially cover for the investigation of the optical frequency response properties of widely diverse selection of workpieces, e.g. a beat frequency from as low as 1 MHz or even lower (assuming that the laser beams have a sufficiently small line width), to as high as about 70 THz or even higher, at which very high frequency the line width of the laser beams is less important, which, as already indicated, permits the use of less expensive lasers.

In connection with this use of a very high beat frequency (in the terahertz range), a further feature of the invention can be employed to overcome the difficulty inherent in the detection of signals at very high frequencies. For example, a frequency of the order of 70 THz is far too high for available devices to detect. In fact, about the maximum frequency that can be detected by typical photomultiplier tubes is of the order of 1–10 GHz. Williams et al. (90) reports measuring the phase and amplitude response of a photodiode up to a frequency of 10 GHz, and Williams et al. (89) reports offset phase-locking of two Nd:YAG nonplanar ring lasers over a tunable range from 6 to 34 GHz, from which it must be deduced that the detector used was able to function at this higher frequency of 34 GHz. Nevertheless, this frequency is about the upper limit of existing detectors, the detection of signals having frequencies in the terahertz range not being presently possible. However, as indicated above, a further feature of the present invention enables this difficulty to be overcome by the effective detection of beat frequencies at least three orders of magnitude higher, e.g. as high as 70 THz. This advancement thus significantly expands the range of the research tool that the arrangement of FIG. 7 represents.

Figure 9:
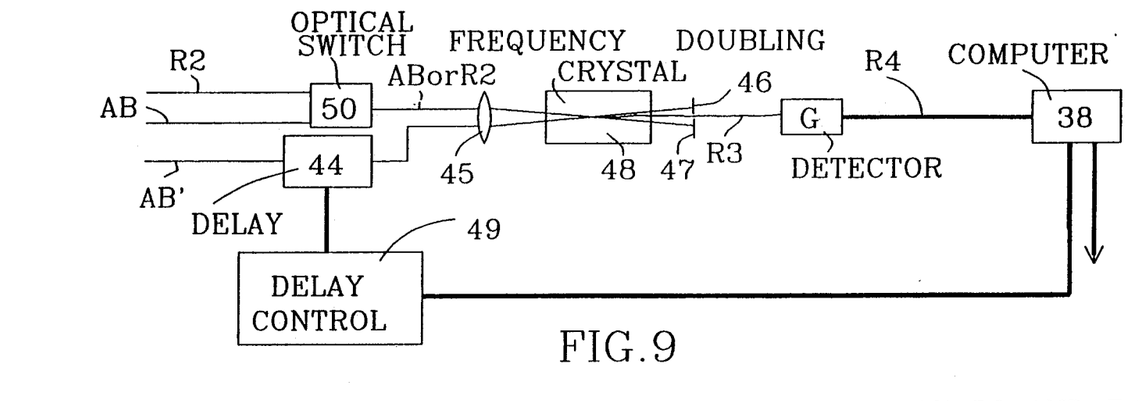
FIG. 9 shows a fragment of an addition to the arrangement of FIG. 7 for carrying out another method according to the invention.

This ability to detect signals at frequencies in the terahertz range is achieved by means of an arrangement shown in FIG. 9 which shows as inputs the similar carrier beams AB and AB' from FIG. 7. The beam AB, is first passed through a delay 44 and is then combined with the beam AB by a lens 45 in a non-linear medium such as a frequency doubling crystal 48, e.g. a potassium diphosphate crystal. This procedure, known as autocorollation, is known in the art. See, for example, "Pulsed Ion and Dye Laser Accessories—Model 409 Scanning Autocorrelator" marketed by Spectra-Physics, and "Model 390 Angle Tuned Frequency Doubler" also marketed by Spectra-Physics. The crystal 48 results in the multiplication together of the two inputs and hence the generation of an output R3 at a new wavelength, typically in the ultraviolet, which output is received in a detector G, e.g. a photo-multiplier tube, that is connected to the computer 38. The original carrier beams AB and AB' are absorbed by stops 46 and 47. The delay 44 can be varied by a control 49. When this delay is such as to produce a phase difference of 0° between the inputs to the crystal 48, the output R3 is as shown at 52 in FIG. 10, assuming that the average intensities of AB' and AB are equal (taken as unity) and that their modulations are a maximum (also taken as unity). Since the detector G cannot respond to a signal of such a high frequency (in the terahertz range), it effectively measures the average value 53 (0.375) of the curve 52 (output R4) and outputs this average value to the computer 38 (or human operator).

Figure 11:
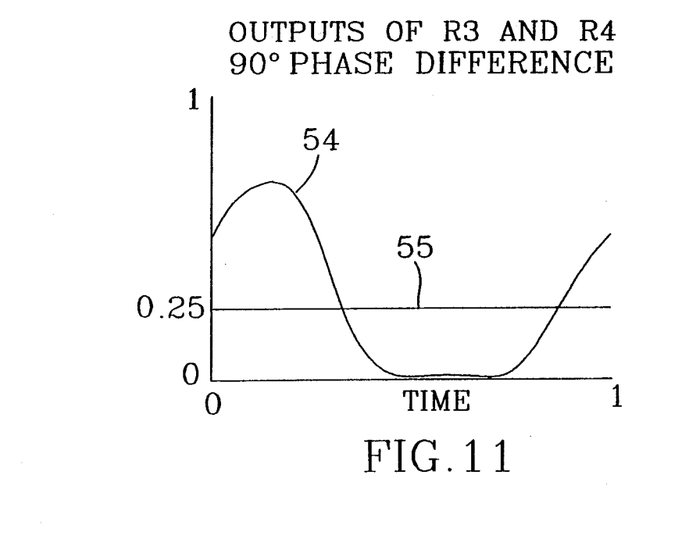

When the phase difference between the two inputs to the crystal 48 is varied by the delay 44 to become 90°, the resultant output R3 is the curve 54 of FIG. 11 and now the detector G measures the average value 55 (output R4) which has a value of 0.25.

Figure 12:
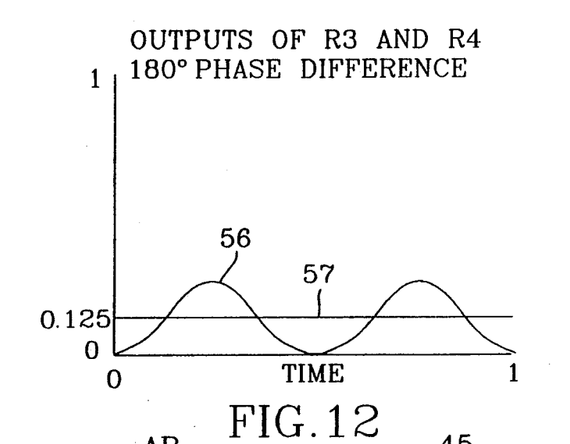

When this phase difference becomes 80°, the curve 56 of FIG. 12 shows the input R3 to the detector G and the line 57 shows its output R4 with an average value of 0.125.

Figure 13:
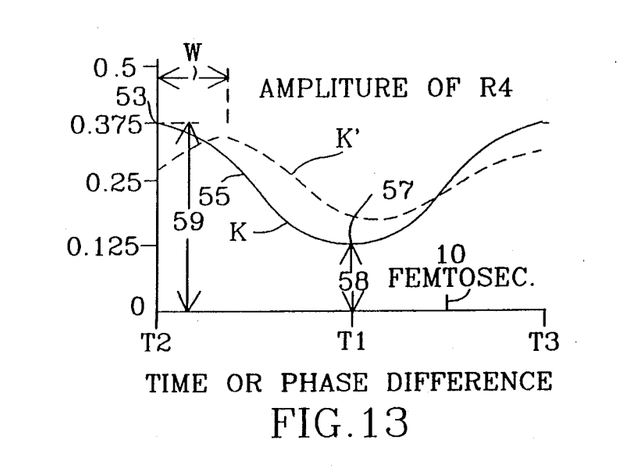

FIG. 13 shows the plot that the computer or human operator can make from these outputs 53, 55 and 57 and as many intermediate points as it is necessary to employ to produce a smooth curve K that represents the output R4 of the detector G as a function of the phase difference between the inputs to the crystal 48. In other words, varying the delay 44, while measuring the output R4 provides the curve K in the output of the computer 38. This curve K can be seen as representing the output R4 plotted against time in femtoseconds ($10^{-15}$ second), i.e. the delay time in the delay 44. When this time is TI for example, the output is a minimum (point 57), and at time T2 it is a maximum (point 53). At a further time T3 it will also be a maximum, the difference T3−T2 representing the period of the beat frequency of the incoming beams. The femtosecond value given in FIG. 13 corresponds approximately to an experimental result obtained with respective beam frequencies of approximately 458 and 528 THz and hence a beat frequency of approximately 70 THz. This arrangement provides an additional method of measuring the value of the beat frequency, as well as having the advantage to be explained below.

Instead of varying the length of the delay 44, the same effect as that just explained can be achieved if this delay is kept constant and the beat frequency is varied by varying one or other or both of the wavelengths A and B. Although the carrier beams AB and AB' have the same beat frequency as each other, since the delay is a fixed time rather than a fixed number of wavelengths, such variation of the beat frequency will change the relative phase of the beams AB and AB' at the crystal 48. In this case, in order to avoid a need to vary the beat frequency excessively, the fixed delay 44 should be equivalent to a relatively large number of wavelengths.

FIG. 9 also shows how this arrangement can be used to overcome the above-mentioned difficulty caused by the inability of standard detectors to detect beat frequencies much above about 30 GHz. In FIG. 9 by means of an optical switch 50 the modulated carrier beam AB is replaced by the modulated response R2 that is received from the workpiece under study, as shown in FIG. 7. This arrangement yields essentially the same shaped plot as the curve K in FIG. 13. The amplitude of the response R4 that the plot K gives is now related to the new second input to the crystal 48, namely the response R2 from the workpiece, which is the response of basic interest.

Figure 10:
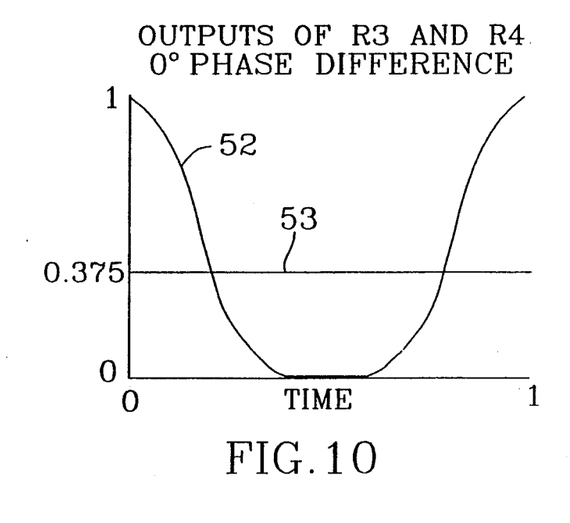
FIGS. 10 to 14 are diagrams illustrating data obtained from the arrangement of FIG. 9.
Figure 14:
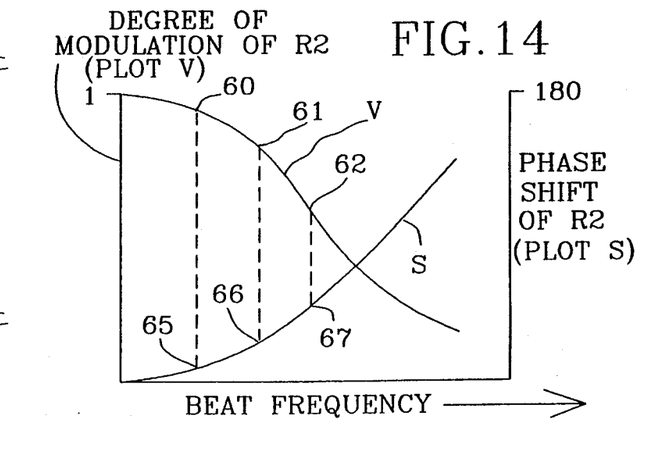

As indicated above, the curves of FIGS. 10 to 12 and hence the plot of FIG. 13 are based on the assumption that the incoming signals AB' and AB (or R2) have maximum modulation. The modulation depth of the curve K, in FIG. 13, i.e. the ratio between the amplitude and the mean value of the maximum and minimum values, is 0.5. This value is half the modulation depth of R2, which was taken as unity. However, in practice, the signal R2 will only be partially modulated (depending on the beat frequency) and this will show up in a corresponding way in the modulation depth of K. If the modulation depth of R2 is for example 0.6, the modulation depth of K will be 0.3. In general, the modulation depth of R2 will be always twice the value of the modulation depth of K, i.e. the modulation depth of R2 can be easily determined from the modulation depth of K. Now, the modulation depth of R2 can be plotted by the computer or other operator as a function of the beat frequency. By noting under one given condition, e.g. a selected beat frequency and an observed modulation depth of K, a point 60 can be generated to start a plot V shown in FIG. 14 for this particular beat frequency. For each other beat frequency the foregoing process must be repeated to generate similar points 61, 62, etc. and hence complete the plot V. This is basically the data desired by the researcher.

Other data that he may desire is the change of phase of the response R2 relative to the beam AB' as a function of the beat frequency. This information can be obtained by initially employing a very low value for the beat frequency and adjusting the delay to produce the plot K. Then, as the beat frequency is increased, which has the effect of shifting the phase of the plot K to a location K' (FIG. 13) by a value W, this change in phase is used as a point 65 to begin a further plot S. By varying the beat frequency as before, points 66, 67 etc. can similarly be obtained to complete the plot S.

The whole procedure can then be repeated, if desired, varying the mean frequency instead of the beat frequency.

As in the case of the generation of plots P and Q (FIG. 8), the generation of plots V and S can, if necessary, be duplicated, for a reference scatterer as well as for the workpiece sample under study.

This autocorollation procedure is equally usable with CW or pulsed lasers, as described above.

Figure 15:
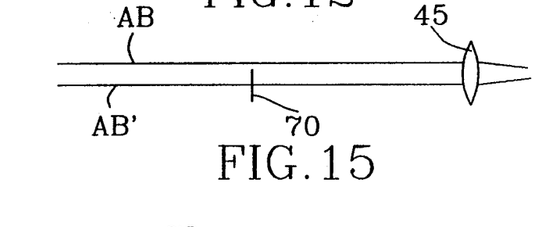
FIGS. 15 and 16 are modified fragments of FIG. 9 each showing an alternative use of the arrangement.

A variation of the arrangement of FIG. 9 and the curves of FIGS. 10-13 can be employed to measure distance, since the length of the delay time in the delay 44 is equivalent to a distance. For example, knowledge of the length of the delay time that the computer receives by virtue of the phase shift W in FIG. 13 can be converted to a distance measurement. For example the delay can be generated by means of a small unknown dimension such as the optical thickness of a thin film 70 as shown in FIG. 15, the remainder of which is assumed to be the same as FIG. 9. The physical thickness of the film 70 can then be derived from the measured phase shift W and the known optical characteristics of the material, i.e. the refractive index. This arrangement constitutes one use of a laser beam modulated at a beat frequency to measure thicknesses.

Figure 16:
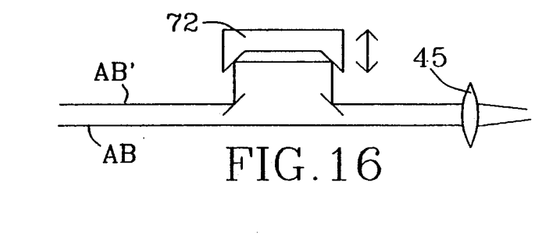

Any variation of the beam path length through air (refractive index approx. =1) will also cause phase shifts related to this change in path length. This can be used for example to measure distances or distance changes of bodies, e.g. the movable body 72 of FIG. 16, reflecting a portion of a beam AB' back to a detector or autocorrelation unit for delay determination (or variation). The best range for use of beat frequencies to measure distances or distance variations will be between 1 micrometer (corresponding to a 3.3 femtosecond delay), and 1 meter (corresponding to a 3.3 nanosecond delay). The respective beat frequency range applied in these cases would be 50 THz (for 1 micrometer) and 50 MHz (for 1 meter). Around and below 1 micrometer interferometer methods are possibly better, and around and above 1 meter pulse delay measurements are relatively easy.

A communications application of the arrangement of FIG. 9 can also be achieved by modifying the way that it is used. Instead of varying the delay 44 for each of a series of given beat frequencies to achieve the curves of FIGS. 10-12 and hence the plot of FIG. 13, as already explained, the delay can be fixed and the beat or mean frequency slightly changed (e.g. a few MHz or less), preferably between a pair of values that correspond respectively to the maximum and minimum points 53 and 57 on the curve K. For example, at a transmitting station the tuner 24 can be controlled by a digital input to the computer 38 to switch the beat frequency back and forth between values that produce these maximum and minimum points 53 and 57, which can now be thought of as the "1" and the "0" of a digital system. The carrier transmission to the receiving station will be by means of the carrier AB, i.e. a very high frequency optical carrier, e.g. at a frequency of 500 THz. The beat frequency, which will now constitute an information sub-carrier, will preferably also have a frequency in the terahertz range, say from 1 THz to 70 THz. Since, as explained above, frequencies in the terahertz range cannot be detected by known detectors, the transmitted beam will represent a communications channel of high security. The transmission can only be decoded at the receiving station by a system such as shown in FIGS. 9-13 which enables detection of the beat frequency and hence whether it represents a "0" or a "1". The rate of data transmission as applied to the switching back and forth of the beat frequency could be as high as can be detected in the signal R3 by the detector G, e.g. up to around 30 GHz. As a further alternative, instead of switching the beat or mean frequency back and forth (frequency modulation), the length of the time delay can be similarly switched back and forth without changing the beat frequency to achieve the same switching between points 53 and 57. This corresponds to a phase modulation at a fixed beat frequency where only a receiving station applying a system such as shown in FIGS. 9-13 can decode the transmission.

We claim:

1. A method of observing an electro-optical frequency response characteristic of a portion of a workpiece, comprising:
   (a) irradiating a molecular (or atomic) population of the workpiece portion with a first laser beam having a first wavelength in a range of approximately 250 to 4000 nm;
   (b) varying this first wavelength to bring it within an absorption curve of the workpiece portion and hence cause elevation of at least some of said population from a first energy level to a second energy level;
   (c) simultaneously irradiating the same workpiece portion with a second laser beam having a second wavelength in the same range but different from the first wavelength;
   (d) detecting the population elevation caused by the first laser beam to form a first response, and thereupon varying the second wavelength to bring it within the same absorption curve of the workpiece portion and hence cause a further molecular (or atomic) population to be elevated from the same first energy level to the same second energy level whereby the combined populations in the second energy level experience irradiation by both beams simultaneously in the form of a carrier beam of a mean frequency halfway between the first and second wavelengths, said carrier beam being amplitude modulated at a beat frequency equal to the difference between the first and second wavelengths;
   (e) detecting this combined population elevation in the form of a second response that is modulated at the beat frequency, and thereupon varying at least one of the first and second wavelengths to vary at least one of the beat frequency and the mean frequency while maintaining both said first and second wavelengths within the absorption curve; and
   (f) measuring at least one characteristic of the second, modulated response as a function of at least one of the beat frequency and the mean frequency to generate data on an electro-optical response characteristic of the workpiece portion.

2. A method according to claim 1, including repeating steps (a) to (f) with a reference workpiece having known response characteristics as a function of at least one of the beat and mean frequencies to obtain data on equipment errors, and compensating for such errors in the measurement of the characteristics obtained from the workpiece under study.

3. A method according to claim 2, wherein the reference workpiece is a scatterer.

4. A method according to claim 1, wherein said step of detecting the population elevation caused by the first laser beam comprises detecting the first response from the workpiece in the form of a secondary optical emission resulting from decay of at least some of the elevated population to a lower energy level, said first response having a characteristic similar to that of the first beam.

5. A method according to claim 1, wherein said step of detecting the modulated beam comprises detecting the second response from the workpiece in the form of a secondary optical emission resulting from decay of at least some of the elevated combined populations to a lower energy level, said second response having the characteristic of being modulated at the beat frequency.

6. A method according to claim 1, wherein said measured characteristic of the second, modulated response includes at least one of the modulation amplitude and the modulation phase of the modulated response as a function of at least one of the beat frequency and the mean frequency.

7. A method according to claim 6, wherein the workpiece portion is fluorescent, and said characteristic provides data on at least one of the fluorescent lifetime and decay of the workpiece portion.

8. A method according to claim 1, wherein said steps of irradiating the workpiece portion with each of the first and second laser beams is performed by preliminarily combining said first and second laser beams into a composite carrier beam modulated at the beat frequency, and irradiating the workpiece portion with said composite beam.

9. A method according to claim 8, including
(g) multiplying the composite modulated carrier beam with a further beam also modulated at the beat frequency, and detecting the average of such multiplication over time;
(h) introducing a shift into the relative phase of the beams being multiplied and varying this phase shift to obtain a plot of different values for said averages as a function of the relative phase; and
(i) ascertaining the maximum and minimum values of said averages.

10. A method according to claim 9, wherein said step of varying the phase shift comprises introducing a variable length time delay into one of the beams being multiplied together, whereby the relationship between said spacing of the maximum and minimum values and the length of the delay provide a measure of the wavelength and hence the frequency of the beat frequency.

11. A method according to claim 9, wherein said step of varying the phase shift comprises introducing a fixed length delay into one of the beams being multiplied together and varying at least one of the beat frequency and the mean frequency, whereby the relationship between said spacing of the maximum and minimum values and the variation in said at least one frequency provides a measure of the length of the delay.

12. A method according to claim 11, including generating the delay with an element of known optical characteristic and calculating the physical thickness of the said element from the measured length of the delay.

13. A method according to claim 9, wherein said further beam is a replica of the composite modulated carrier beam.

14. A method according to claim 9, wherein said further beam is the second response from the workpiece portion, the method including the further step of measuring the degree of modulation of said second response by measuring the modulation depth of said plot of the different values for said averages, said modulation depth being given by the ratio between the amplitude of, and the mean value of, said maximum and minimum values.

15. A method according to claim 14 including repeating the step of measuring the degree of modulation of the second response while varying at least one of the beat frequency and the mean frequency, whereby to generate at least one of a plot of said degree of modulation of the second response and a plot of the phase shift of said modulation of the second response as a function of said at least one frequency.

16. A method according to claim 9, wherein said further beam is the second response from the workpiece portion, the method including varying at least one of the beat frequency and the mean frequency, and observing a corresponding shift in phase of the plot of different values for said averages and establishing a further plot of such phase shifts as a function of said at least one frequency.

17. A method according to claim 9, including multiplying a pair of like versions of said composite modulated carrier beam together and detecting the average of such multiplication over time; introducing a time delay into one of the beams being multiplied together and again detecting the average of such multiplication over time; digitally switching back and forth at least one of the beat frequency, the mean frequency and the length of the time delay in order to introduce a relative phase shift into the beams being multiplied to obtain different values for said averages, said different values representing the respective digital values.

18. A method of observing an electro-optical frequency response characteristic of a workpiece, comprising
(a) irradiating a molecular (or atomic) population of a portion of the workpiece with first and second laser beams respectively having first and second wavelengths both in a range of approximately 250 nm to approximately 4000 nm whereby to subject said population to a composite carrier beam of a mean frequency midway between the first and second wavelengths, said carrier beam being amplitude modulated at a beat frequency equal to the difference between the first and second wavelengths whereby to obtain from said population a response beam modulated at the beat frequency;
(b) multiplying the composite modulated carrier beam with said response beam and detecting the average of such multiplication over time;
(c) introducing a variable length time delay into one of the beams to cause a shift in the relative phase of the carrier and response beams and varying this length to obtain a plot of different values for said averages as a function of the relative phase;
(d) ascertaining the maximum and minimum values of said averages; and
(e) measuring the degree of modulation of said response beam by measuring the modulation depth of said plot of the different values for said averages, said modulation depth being given by the ratio between the amplitude of, and the mean value of, said maximum and minimum values.

19. A method according to claim 18, including repeating the step of measuring the degree of modulation of the response beam while varying at least one of the beat frequency and the mean frequency, whereby to generate at least one of a plot of said degree of modulation of the response beam and a plot of the phase shift of said modulation of the response beam as a function of said at least one frequency.

20. A method of measuring a beat frequency of two laser beams of different wavelength, comprising
(a) combining first and second laser beams respectively having first and second wavelengths both in a range of approximately 250 nm to approximately 4000 nm but different from each other to generate a carrier beam of a mean frequency halfway between the first and second wavelengths, said carrier beam being modulated at a beat frequency equal to the difference between the first and second wavelengths;

(b) splitting said carrier beam into two portions;

(c) multiplying said two beam portions together and detecting the average of such multiplication over time;

(d) introducing a shift into the relative phase of the beam portions and varying this phase shift to obtain a plot of different values for said averages as a function of the relative phase; and (e) measuring the spacing between two consecutive maximum or minimum values of said averages to measure the beat frequency.

21. A method according to claim 20, wherein the step of varying the phase shift comprises introducing a variable length time delay into one of the beam portions.

22. A method according to claim 20, wherein the step of varying the phase shift comprises varying the mean frequency.

23. A method of measuring distance comprising (a) combining first and second laser beams respectively having first and second wavelengths both in a range of approximately 250 nm to approximately 4000 nm but different from each other to generate a carrier beam of a mean frequency halfway between the first and second wavelengths, said carrier beam being modulated at a beat frequency equal to the difference between the first and second wavelengths;

(b) splitting said carrier beam into two portions;

(c) multiplying said two beam portions together and detecting the average of such multiplication over time;

(d) locating said distance in one of said beam portions to introduce a relative phase shift between the beam portions being multiplied and obtaining a further average of the multiplication with said phase shift applied to the beam portions; and (e) comparing the value of this further average with the value of the average obtained without the phase shift to determine the length of the phase shift and hence said distance.

24. A method according to claim 23, wherein said distance is constituted by the thickness of an element of known optical characteristics.

25. A method according to claim 23, wherein said distance is constituted by a beam path length interposed in one of said beams.

26. A method of communication comprising (a) combining first and second laser beams respectively having first and second wavelengths both in a range of approximately 250 nm to approximately 4000 nm but different from each other to generate a carrier beam of a mean frequency halfway between the first and second wavelengths, said carrier beam being modulated at a beat frequency equal to the difference between the first and second wavelengths;

(b) splitting said carrier beam into two portions;

(c) multiplying said two beam portions together and detecting the average of such multiplication over time;

(d) introducing a time delay into one of the beam portions being multiplied together; and (e) digitally switching back and forth at least one of the beat frequency, the mean frequency and the length of the time delay to introduce a relative phase shift into the beam portions being multiplied to obtain different values for said averages that represent the respective digital values.

27. Apparatus for observing an electro-optical frequency response characteristic of a workpiece, comprising (a) a pair of lasers for subjecting a molecular (or atomic) population of a portion of the workpiece to a composite carrier beam of a mean frequency midway between wavelengths of the lasers amplitude modulated at a beat frequency equal to a difference between said wavelengths to obtain from said population a response beam modulated at the beat frequency;

(b) means for multiplying the composite carrier beam with said response beam, including means for detecting the average of such multiplication over c) time delay means located in one of said beams;

(d) means for varying the length of said time delay and for plotting different values for said averages for different lengths of time delay; and (e) means for measuring the modulation depth of said plot for the different values of said averages as a ratio between the amplitude of, and the mean value of, the maximum and minimum values of, said plot to provide a measure of the degree of modulation of the response beam.

28. Apparatus according to claim 27, including means associated with the lasers for varying at least one of the beat frequency and the mean frequency for plotting at least one of said degree of modulation of the response beam and a phase shift of said modulation of the response beam as a function of said at least one frequency.

29. Apparatus for measuring distance, comprising (a) a pair of lasers for generating a composite carrier beam of a mean frequency midway between wavelengths of the lasers amplitude modulated at a beat frequency equal to a difference between said wavelengths;

(b) means for splitting said composite beam into two portions;

(c) means for multiplying said two beam portions together and for detecting the average of such multiplication over time;

(d) means for locating said distance in one of said beam portions to introduce a relative phase shift between the beam portions being multiplied for obtaining a further average of the multiplication with said phase shift applied to the beam portions; and (e) means for comparing the value of this further average with the value of the average obtained without the phase shift for determining the value of the phase shift and hence said distance.

30. Apparatus according to claim 29, wherein said distance is constituted by the thickness of an element of known optical characteristics.

31. Apparatus according to claim 29, wherein said distance is constituted by a beam path length interposed in one of said beam portions.

32. Apparatus for digital transmission of data on a laser beam, comprising (a) a pair of lasers for generating a composite carrier beam of a mean frequency midway between wavelengths of the lasers amplitude modulated at a beat frequency equal to a difference between said wavelengths;
(b) means for splitting said composite beam into two portions;
(c) means for multiplying said two beam portions together and for detecting the average of such multiplication over time;
(d) digital input means for switching back and forth at least one of the beat frequency, the mean frequency and the length of the time delay for introducing a relative phase shift into the beam portions being multiplied to obtain different values for said averages that represent the respective digital values.

* * * * *